(12) United States Patent
Ritter

(10) Patent No.: US 8,183,418 B2
(45) Date of Patent: *May 22, 2012

(54) PROCESS FOR THE SYNTHESIS OF DIHALODINITROTOLUENE

(75) Inventor: Joachim C. Ritter, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,772

(22) Filed: Dec. 10, 2009

(65) Prior Publication Data

US 2010/0160695 A1 Jun. 24, 2010

Related U.S. Application Data

(60) Provisional application No. 61/138,672, filed on Dec. 18, 2008.

(51) Int. Cl.
*C07C 205/00* (2006.01)

(52) U.S. Cl. ........................................................ 568/933

(58) Field of Classification Search .................. 568/933
See application file for complete search history.

(56) References Cited

FOREIGN PATENT DOCUMENTS

| EP | 237955 | | 7/1992 |
|---|---|---|---|
| JP | 07048321 | * | 2/1995 |
| JP | 2003-292475 | | 10/2003 |

OTHER PUBLICATIONS

Blanksma, Nitro Derivatives of 2,6-Dibromotoluene, Chemisch Weekblad, 1913, vol. 9, pp. 968-973, Abstract Only.
Knobloch et al., Synthesis of 2.6-Disubstituted Benzo (1.2.4.5) Bisimidazol, Chemische Berichte, 1958, vol. 91, pp. 2562-2565 (Machine Translated).
Ritter et al., U.S. Appl. No. 61/138,602, filed Dec. 18, 2008.
Ritter et al., U.S. Appl. No. 61/138,615, filed Dec. 18, 2008.
Dhawan et al., U.S. Appl. No. 61/138,626, filed Dec. 18, 2008.
Dhawan et al., U.S. Appl. No. 61/138,678, filed Dec. 18, 2008.
Dhawan et al., U.S. Appl. No. 61/138,651, filed Dec. 18, 2008.
Dhawan et al., U.S. Appl. No. 61/138,696, filed Dec. 18, 2008.
Dhawan et al., U.S. Appl. No. 61/138,662, filed Dec. 18, 2008.

* cited by examiner

*Primary Examiner* — Jafar Parsa
(74) *Attorney, Agent, or Firm* — Kevin S. Dobson

(57) ABSTRACT

An improved process is provided for the preparation of 2,6-dihalo-3,5-dinitrotoluene by the nitration of 2,6-dihalotoluene. The direct isolation of highly pure 2,6-dihalo-3,5-dinitrotoluene is accomplished without a water or ice quench, by providing at least one equivalent of $SO_3$ during the reaction, slow crystallization, and isolation of product from a cold crystal slurry.

9 Claims, No Drawings

PROCESS FOR THE SYNTHESIS OF DIHALODINITROTOLUENE

This application claims priority under 35 U.S.C. §119(e) from, and claims the benefit of, U.S. Provisional Application No. 61/138,672, filed Dec. 18, 2008, which is by this reference incorporated in its entirety as a part hereof for all purposes.

TECHNICAL FIELD

The disclosure relates to a method of making 2,6-dihalo-3,5-dinitrotoluene, which may be used in the manufacture of dyes, pharmaceuticals, pesticides, agrochemicals and polymers.

BACKGROUND

The compound 2,6-dihalo-3,5-dinitrotoluene ("DHDNT") (I),

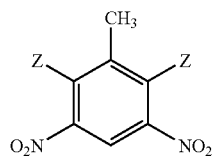

(I)

wherein Z is Br or Cl, may be used as a starting material or intermediate in the preparation of a variety of products, which include dyes, pharmaceuticals, pesticides, agrochemicals, and monomers for incorporation into polymers.

Known processes for the preparation of DCDNT

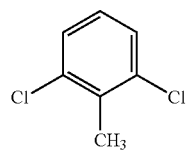

(II)

(see, e.g., EP 237,955) require a costly work-up procedure ("quench") wherein the product and a sulfuric acid reaction mixture is added to a large quantity of ice and/or diluted with 5-10 times the volume of water. The large volumes, the difficulties of managing the exotherm associated with this quench procedure, and the difficulty of recycling the sulfuric acid result in considerable fixed and variable cost.

It would be desirable to eliminate the need for a quench procedure in the preparation of a compound such as DHDNT, and a need thus remains for an improved process for making compounds of Formula (I), particularly 2,6-dichloro-3,5-dinitrotoluene ("DCDNT"), with improved selectivity and high purity.

SUMMARY

In one embodiment, this invention provides a process for preparing 2,6-dihalo-3,5-dinitrotoluene comprising the sequential steps:
a) preparing a reaction mixture by combining fuming nitric acid; sulfuric acid; oleum or $SO_3$; and 2,6-dihalotoluene (III)

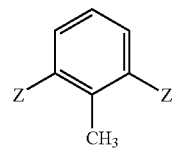

III wherein each Z is independently Cl or Br;
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene; and
(iii) the concentration of 2,6-dihalotoluene in the reaction mixture is between about 12 and about 24 weight percent;
wherein the temperature of the reaction mixture does not exceed 120° C.;
b) optionally, heating the reaction mixture at a temperature not to exceed about 120° C., then cooling the reaction mixture or allowing it to cool;
c) allowing reaction to proceed to completion with stirring at a temperature between about −10° C. and about 70° C.; and
d) isolating the product 2,6-dihalo-3,5-dinitrotoluene from the reaction mixture at a temperature between about 0° C. and about 40° C.

DETAILED DESCRIPTION

The following description is exemplary and explanatory only and is not restrictive of the invention, as defined in the appended claims.

One embodiment of this invention provides a process for preparing 2,6-dihalo-3,5-dinitrotoluene comprising the sequential steps:
a. preparing a reaction mixture by combining nitric acid; sulfuric acid; oleum or $SO_3$; and 2,6-dihalotoluene (III)

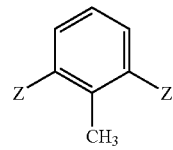

III wherein each Z is independently Cl or Br;
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene; and
(iii) the concentration of 2,6-dihalotoluene in the reaction mixture is between about 12 and about 24 weight percent; and
wherein the temperature of the reaction mixture does not exceed 120° C.;
b. optionally, heating the reaction mixture at a temperature not to exceed about 120° C., then cooling the reaction mixture or allowing it to cool;
c. allowing reaction to proceed to completion with stirring at a temperature between about −10° C. and about 70° C.; and d. isolating the product 2,6-dihalo-3,5-dinitrotoluene from a crystal slurry at a temperature between about 0° C. and about 40° C.

Unexpectedly, isolating the crystalline product directly from the reaction mixture, without water quenching and subsequent crystallization steps, gives a high purity product.

In another embodiment, the process further comprises isolating the product 2,6-dihalo-3,5-dinitrotoluene from the reaction mixture in step (d) by filtration, leaving a filtrate, wherein the filtrate comprises sulfuric acid and additional desired product; extracting the additional desired product from the filtrate, leaving an extracted filtrate comprising sulfuric acid; and recycling the extracted filtrate for use in the production of additional 2,6-dihalo-3,5-dinitrotoluene.

In the context of this disclosure, a number of terms shall be utilized.

As used herein, the term "oleum" denotes fuming sulfuric acid, which is anhydrous and is formed by dissolving excess sulfur trioxide ($SO_3$) into sulfuric acid.

As used herein, the term "fuming nitric acid" denotes concentrated nitric acid containing dissolved nitrogen dioxide.

As used herein, the term "net yield" of a product denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

The concentration of nitric acid in the reaction mixture is about 2.0 to about 2.3 moles per mole of 2,6-dihalotoluene ("mDHT"). Concentrated nitric acid (e.g., commonly used reagent grade, which is about 70% nitric acid in water) can be used, but fuming nitric acid is preferred. If concentrated nitric acid is used, since in the process described herein water must be kept at a level below one equivalent to get highly pure product, more $SO_3$ would be added to remove the water from the nitric acid (by reacting with it to form sulfuric acid) and still have sufficient $SO_3$ present in the reaction mixture for the nitration reaction. The amount of $SO_3$ in the reaction mixture is about 1 to about 3 moles, preferably 1.5 to 2 moles, per mole of mDHT. The sulfuric acid is present in an amount such that the weight percent of mDHT in the reaction mixture (i.e., the weight of mDHT relative to the combined weight of mDHT plus the acid solution) is between 12 and 24 weight percent.

2,6-dibromotoluene, 2,6-dichlorotoluene, and 2-bromo-6-chlorotoluene are all commercially available, for example, from Alfa Aesar (Ward Hill, Mass., USA).

The sulfuric acid, oleum or $SO_3$, and nitric acid may be combined with the mDHT in any possible addition mode, excluding those in which the mDHT is premixed with nitric acid or oleum or $SO_3$ before adding it to the reaction vessel and those in which mDHT and oleum or $SO_3$ are combined in the reaction vessel before nitric acid is added. Premixing the mDHT with nitric acid would cause undesirable reaction. Contacting mDHT with oleum or $SO_3$ in the absence of nitric acid would cause undesirable sulfonic acids to form irreversibly.

Examples of possible addition modes include, but are not limited to, adding mDHT to a mixture of nitric acid and sulfuric acid containing between 1 and 3 mol equivalents of $SO_3$ per mol equivalent of mDHT; adding a mixture of oleum and nitric acid to a mixture of mDHT and an optional amount of sulfuric acid; adding mDHT and oleum separately but concurrently to nitric acid; and adding mDHT and a mixture of oleum and nitric acid separately but concurrently to sulfuric acid.

The addition of solution components can be controlled such that the reaction mixture temperature during the addition stays below 120° C., preferably below 60° C., and most preferably between −10° and +15° C. The rate at which the mDHT is added will depend on, e.g., the reaction temperature, the efficiency with which the reaction vessel can be cooled, and the batch size. Typical addition times may be about 30 minutes to several hours. Addition time greatly depends on the cooling capacity and heat transfer coefficient of the equipment used and is readily determined using standard calorimetric and engineering methodology, as known to those skilled in the art.

Furthermore, to produce a product of high purity, the accumulation of more than 1 mol equivalent of water throughout the reaction can be avoided. This can be achieved by adding at least 1 mol equivalent of a suitable water removing agent. The most suitable water removing agent in this case is $SO_3$. Preferably, 1.5-2.25 mol equivalents of $SO_3$ are introduced as described above to achieve the isolation of high purity 2,6-dihalo-3,5-dinitrotoluene. Under these circumstances, all impurities, including any undesired isomer, remain in solution; and crystalline 2,6-dihalo-3,5-dinitrotoluene of >99% purity is isolated at high yields.

The temperature is maintained between about −10° and about 40° C., preferably between about 0° and about 25° C. while stirring for an additional time period, typically a few hours, until the reaction is completed and no more reaction heat is generated. Slow crystallization occurs as the DHDNT is precipitated. The slow crystallization results in a high-purity product.

In an optional step, the reaction mixture temperature is increased following the completion of addition of all components to convert small amounts of starting materials and intermediates to product. This step is intended to shorten the time to reaction completion by removing trace amounts of intermediates. The specific reaction set-up used will determine whether or not this heating step is more productive than just stirring for a few hours as described above; this is readily determined by one skilled in the art. In this optional step, it is preferred not to exceed a temperature of 120° C., more preferred not to exceed 85° C. Heating rates will depend on, e.g., the efficiency with which the reaction vessel can be heated and the batch size. Typical heating times may be about 30 minutes to several hours. Reaction is allowed to occur at the elevated temperature for a short time, typically about 10 minutes to about an hour. The reaction mixture is then cooled, or allowed to cool, to between about 70° and about 30° C. to allow slow crystallization as the DHDNT product is precipitated. The slow crystallization results in a high-purity product.

The product can then be isolated from a cold crystal slurry. The preferred isolation temperature for the 2,6-dihalo-3,5-dinitrotoluene product depends on its concentration and on the amount of impurities present, but is generally chosen between about 0° and about 40° C. For a 2,6-dihalo-3,5-dinitrotoluene concentration of up to about 20% by weight, the most preferred isolation temperature is between about 0° and about 10° C.

Controlling the feed rate and reaction temperature allows for increased selectivity, greater than 95% for 2,6-dichloro-3,5-dinitrotoluene specifically. The direct isolation of highly pure 2,6-dihalo-3,5-dinitrotoluene is accomplished without a water or ice quench, by providing at least one equivalent of $SO_3$ during the reaction, slow crystallization, and isolation of product from a cold crystal slurry. This allows for the isolation of high-purity product. The process described herein thereby produces 2,6-dichloro-3,5-dinitrotoluene of >99% purity at a typical net yield of 90%.

In another embodiment, the process further comprises isolating the product 2,6-dihalo-3,5-dinitrotoluene from the reaction mixture in step (d) by filtration, leaving a filtrate, wherein the filtrate comprises sulfuric acid and additional desired product; extracting the additional desired product from the filtrate, leaving an extracted filtrate comprising sulfuric acid; and recycling the extracted filtrate (the "sulfuric acid mother liquor") for use in the production of more 2,6-dihalo-3,5-dinitrotoluene, a representative scheme for which is shown below:

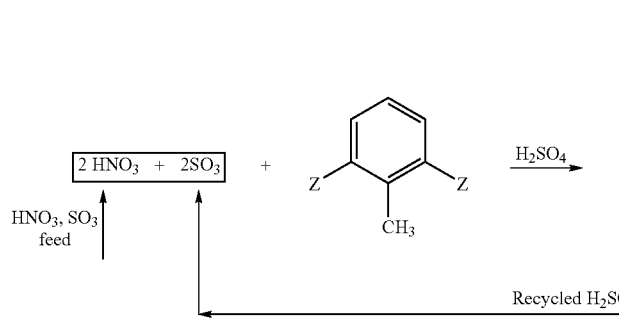
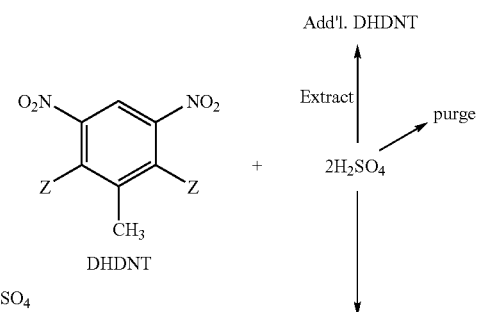

The additional DHDNT is recovered by extracting the $H_2SO_4$ with, e.g., toluene. Such extraction is carried out at about room temperature to avoid reaction. The DHDNT is precipitated and the toluene is reused. The extracted sulfuric acid mother liquor is directly recycled without water quench. Because $H_2SO_4$ is continually produced, a purge (about 10%) is withdrawn as shown.

In the process described herein, the product and sulfuric acid reaction mixture is not added to a large quantity of ice, nor diluted with 5-10 times the volume of water. As a consequence, the volume of recyclable sulfuric acid mother liquor generated is much lower than in previous processes.

In the process described herein, highly pure product is produced at high selectivity and net yield. The large volumes, difficulties of managing the exotherm associated with a water or ice quench procedure and the difficulties for recycling the sulfuric acid characteristic of previous processes are avoided in the process described herein, resulting in considerable fixed and variable cost savings.

The materials, methods, and examples herein are illustrative only and, except as specifically stated, are not intended to be limiting.

EXAMPLES

This invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The meaning of abbreviations is as follows: "d" means density, "equiv" means equivalent(s), "g" means gram(s), "GC" means gas chromatography, "$^1$H-NMR" means proton nuclear magnetic resonance spectroscopy, "h" means hour(s), "L" means liter(s), "mL" means milliliter(s), "min" means minutes, and "mol" means mole(s).

Example 1

This example demonstrates the preparation of 2,6-dichloro-3,5-dinitrotoluene from 2,6-dichlorotoluene according to the process described herein.

To a 1 L 3-neck round bottom flask equipped with external ice cooling, mechanical stirrer, addition funnel, $N_2$ inlet, and thermometer was added 174 g (2.76 mol) fuming nitric acid (d=1.54), followed by 350 g sulfuric acid and 659 g 30% oleum (2.0 molar equiv $SO_3$) maintaining a temperature between 5° C. and 20° C. Subsequently, 199 g (1.23 mol) 2,6-dichlorotoluene (Aldrich Chemical Company, Milwaukee, Wis., USA, 99% purity) were added over a time period of 3 hours while maintaining a temperature between 0° C. and 10° C. The ice bath was removed, and the reaction mixture was allowed to warm up to room temperature. It was then heated to 100° C. for about 2 h.

To analyze the reaction mixture, a small sample of crude product was taken from the reaction vessel and poured into ice water. The crude product was extracted with methylene chloride. Analysis by GC indicated a reaction selectivity to 2,6-dichloro-3,5-dinitrotoluene of >97%. Subsequently, the reaction mixture was allowed to cool to room temperature over 2 h and then cooled to 5° C. over 30 min, after which it was filtered through a glass fritted funnel and washed with a little sulfuric acid followed by 200 mL $H_2O$. After drying, 291 g of >99.5% pure product (by $^1$H-NMR) were isolated (93.5% yield).

Comparative Example A

This example demonstrates the preparation of 2,6-dichloro-3,5-dinitrotoluene from 2,6-dichlorotoluene using a nitration method as reported previously and isolating the product after quenching the reaction mixture with a large quantity of ice water.

To a 500 mL 4-neck round bottom flask equipped with external ice cooling, mechanical stirrer, addition funnel, $N_2$ inlet, and thermometer was added 150 g (82 mmol) concentrated sulfuric acid. With vigorous stirring and cooling, 25 g 2,6-dichlorotoluene (155 mmol) was added over a period of 20 minutes while maintaining a temperature 0-5° C. 25 g (391 mmol) fuming nitric acid was then slowly added over 2 hrs. while maintaining a temperature below 20° C. The ice bath was removed, and the reaction mixture was slowly allowed to warm to room temperature. It was then stirred at room temperature for one hour, and then heated to 45° C. for three hours. After cooling to room temperature it was poured over 500 g of ice and filtered through a glass fritted funnel. The filter cake was washed with 25 mL water followed by 25 mL 10% aqueous NH$_3$ solution. After drying, 34.8 g of material were isolated containing about 1% 2,6-dichloro-4,5-dinitrotoluene, 2.5% 2,6-dichloro-3-nitrotoluene and 96.5% of the desired product, 2,6-dichloro-3,5-dinitrotoluene. The net yield was 89%.

Recrystallization of the crude product from a saturated solution in ethanol improved purity to 98-99%, but the net yield was less than 80%.

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

What is claimed is:

1. A process for preparing 2,6-dihalo-3,5-dinitrotoluene comprising the sequential steps:

a) preparing a reaction mixture by combining fuming nitric acid; sulfuric acid; oleum or SO3; and 2,6-dihalotoluene (III)

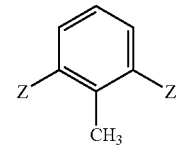

III wherein each Z is independently Cl or Br;
wherein
(i) the concentration of nitric acid is about 2.0 to about 2.3 moles per mole of 2,6-dihalotoluene;
(ii) the concentration of SO3 is about 1 to about 3 moles per mole of 2,6-dihalotoluene; and
(iii) the concentration of 2,6-dihalotoluene in the reaction mixture is between about 12 and about 24 weight percent;
wherein the temperature of the reaction mixture does not exceed 120° C.;
b) optionally, heating the reaction mixture at a temperature not to exceed about 120° C., then cooling the reaction mixture or allowing it to cool;
c) allowing reaction to proceed to completion with stirring at a temperature between about −10° C. and about 70° C.; and
d) isolating the product 2,6-dihalo-3,5-dinitrotoluene from the reaction mixture at a temperature between about 0° C. and about 40° C., wherein isolating the product is achieved by filtration of the reaction mixture without water quenching.

2. The process of claim 1 wherein the concentration of SO$_3$ is about 1.5 to about 2 moles per mole of 2,6-dihalotoluene.

3. The process of claim 1 wherein the temperature of the reaction mixture in step (a) is between about −10° C. and about +15° C.

4. The process of claim 1 wherein the reaction is allowed to proceed to completion in step (c) at a temperature between about 0° and about 25° C.

5. The process of claim 1 wherein the 2,6-dihalo-3,5-dinitrotoluene concentration in the reaction mixture in step (d) does not exceed about 20% by weight and the 2,6-dihalo-3,5-dinitrotoluene is isolated at a temperature between about 0° and about 10° C.

6. The process of claim 1 wherein the reaction mixture is prepared by adding 2,6-dihalotoluene to a mixture of fuming nitric acid, oleum, and sulfuric acid; by adding a mixture of oleum and fuming nitric acid to a mixture of 2,6-dihalotoluene and sulfuric acid; by adding 2,6-dihalotoluene and oleum separately but concurrently to fuming nitric acid; or by adding 2,6-dihalotoluene and a mixture of oleum and fuming nitric acid separately but concurrently to sulfuric acid.

7. The process of claim 1 further comprising extracting additional desired product from the filtrate, leaving an extracted filtrate comprising sulfuric acid.

8. The process of claim 7 further comprising recycling the extracted filtrate for use in the production of additional 2,6-dihalo-3,5-dinitrotoluene.

9. The process of claim 1 wherein the reaction is run for about 10 min to about 1 hour.

* * * * *